United States Patent [19]

Copp et al.

[11] 4,277,498
[45] Jul. 7, 1981

[54] AMIDES

[75] Inventors: Frederick C. Copp; David Collard, both of Beckenham; Clive V. Denyer, London, all of England

[73] Assignee: Burroughs Wellcome Co., Research Triangle Park, N.C.

[21] Appl. No.: 59,955

[22] Filed: Jul. 23, 1979

Related U.S. Application Data

[62] Division of Ser. No. 810,610, Jun. 27, 1977, abandoned.

[30] Foreign Application Priority Data

Jun. 28, 1976 [GB] United Kingdom ............... 26794/76
May 26, 1977 [GB] United Kingdom ............... 22204/77

[51] Int. Cl.$^3$ ............................................. A61K 31/16
[52] U.S. Cl. .................................. 424/320; 424/303; 424/317; 260/501.17; 260/544 Y
[58] Field of Search .......... 260/561 A, 544 Y, 501.17; 424/320

[56] References Cited

U.S. PATENT DOCUMENTS 3,223,700  12/1965  Klavehn et al. ................. 260/561 A

FOREIGN PATENT DOCUMENTS 256032   5/1963  Australia .
1322069  7/1973  United Kingdom .

Primary Examiner—Patrick Garvin
Assistant Examiner—J. V. Howard
Attorney, Agent, or Firm—Donald Brown

[57] ABSTRACT

Glycinamides of formula (1):

$$NH_2CH_2CONHE \qquad (1)$$

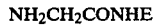

wherein E has seven to nine carbon atoms and is branched alkyl, alkylcycloalkyl or cycloalkylalkyl or their acid addition salts, methods of preparing them, pharmaceutical compositions containing them and their use in medicine as anti-depressants.

44 Claims, No Drawings

AMIDES

This is a division of application Ser. No. 810,610 filed June 27, 1977 now abandoned.

This invention relates to novel glycinamides and processes for their preparation, intermediates and processes for their preparation, pharmaceutical formulations containing them, methods for producing such formulations and to their use in medicine.

In particular the present invention relates to glycinamides of formula (I):

NH₂CH₂CONHE  (I)

and acid addition salts thereof wherein E has seven to nine carbon atoms and is selected from alkylcycloalkyl, cycloalkylalkyl and branched alkyl. Except when there is clear indication to the contrary, formula (I) and all other formulae in the specification embrace all the stereoisomers represented therein. In particular such formulae include all optical isomers, racemic mixtures and diastereomers possible.

When used in medicine the salts of a compound of formula (I) should be both pharmacologically and pharmaceutically acceptable acid addition salts, but non-acceptable salts may be conveniently used to prepare the bases of such acceptable salts and are not excluded from the scope of this invention. Acceptable salts may be derived from organic acids, particularly dicarboxylic acids. Such pharmacologically and pharmaceutically acceptable salts include those prepared from the following acids: hydrochloric, hydrobromic, sulphuric, nitric, succinic, toluene-p-sulphonic, tartaric, acetic, citric, methanesulphonic, formic, benzoic, malonic, naphthalene-2-sulphonic and benzenesulphonic.

The compounds of formula (I) and their acid addition salts exhibit antidepressant properties in mammals when tested by standard techniques for example the tetrabenazine-induced sedation test in the rat.

Some of the potent compounds of formula (I) are encompassed by formula (II):

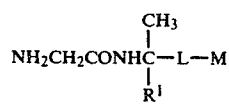

wherein E is a group of formula (III):

wherein
R¹ is hydrogen or methyl;
L is alkylene;
M is alkyl or cycloalkyl; or
the group (III) forms a cycloalkyl residue,

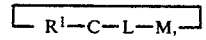

and E has seven to nine carbon atoms.

Especially potent activity is found in these compounds of formula (II) wherein E has seven to eight carbon atoms, L is unbranched alkylene and wherein M is cycloalkyl or unbranched alkyl.

Acceptable salts of the following compounds have shown antidepressant activity in the tetrabenazine-induced sedation test:
2-amino-N-(1-methylhexyl)acetamide;
2-amino-N-(2-cyclopentyl-1,1-dimethylethyl)acetamide and
2-amino-N-(1,1,5-trimethylhexyl)acetamide.

The preferred glycinamide of this invention is 2-amino-N-(1,1-dimethylhexyl)acetamide and acceptable acid addition salts thereof.

The compounds of formula (I) may be synthesized by any known method for preparing compounds of analogous structure, and particularly by formation of the amino group; by demasking a protected amino group or by the formation of the amido linkage.

Suitable methods for preparing the compounds of formula (I) by the formation of the primary amine residue include reacting a compound of formula (IV):

JCH₂CONHE  (IV)

with ammonia, wherein E is as defined in formula (I) hereinabove and J is a leaving group selected from for example halo, alkanesulphonyloxy, arenesulphonyloxy and alkylarenesulphonyloxy; preferably chloro, bromo and toluene-p-sulphonyloxy. The reaction may be conveniently be carried out in a polar solvent such as an alkanol or an alkanol-water mixture. Alternatively (IV) may be reacted with hexamethylenetetramine and the intermediate product hydrolysed under acidic conditions to give the desired compound of formula (I). These displacement reactions may be effected at a temperature in the range of 0° C. ot 120° C.

The compounds of formula (I) may conveniently be prepared by deprotection of a derivative of a compound of formula (I) wherein the amino group is protected or masked. Suitable protected or masked amino derivatives include compounds of formula (V):

QCH₂CONHE  (V)

wherein E is as defined in formula (I) hereinabove and Q may be selected from nitro, azido, NHX and N=Y; wherein X is selected from alkanoyl, halogenated alkanoyl such as trifluoroacetyl, aroyl such as benzoyl, aralkyl such as benzyl or trityl, aralkoxycarbonyl such as benzyloxycarbonyl, alkoxycarbonyl such as t-butoxycarbonyl, arenesulphonyl such as benzenesulphonyl, alkylarenesulphonyl such as tosyl, and trimethylsilyl; and wherein Y is selected from aralkylidene such as benzylidene, alkylidene such as methylidene, diacyl radicals derived from arene dicarboxylic acids such as phthalic acid and diacyl radicals derived from alkane dicarboxylic acids such as succinic acid.

Other protecting groups known in the art may also be used as described, for example, in "Protective Groups in Organic Chemistry", 1973, Edited by J. F. W. McOmie, Plenum Press, p. 43–93 and references therein.

The protecting group may be removed by any suitable method known in the art. When the group is a formyl, trityl, alkoxycarbonyl, trimethylsilyl, alkylidene or aralkylidene moiety the deprotection may conveniently be effected in acid conditions, preferably by reaction with a dilute mineral acid in a polar solvent such as an alkanol, water or an alkanol-water mixture at the reflux temperature of the reaction mixture. Groups such as alkanoyl, halogenated alkanoyl, aroyl, and diacyl radicals derived from alkane- or arene-dicarboxylic acids may conveniently be removed under basic conditions by treatment with hydrazine, ammonia, an alkali metal hydroxide, an alkali metal hydride, an alkali metal amide or an alkali metal alkoxide in a polar solvent such as an alkanol, water or an alkanol-water mixture at the reflux temperature of the reaction mixture. When the group Q is a nitro, azido, aralkoxycarbonylamino or aralkylamino group the deprotection may conveniently be effected in a polar solvent such as an alkanol by hydrogenation of the derivative in the presence of a catalyst, such as palladium, at a temperature in the range of 0° C. to 100° C. Arenesulphonyl or alkylarenesulphonyl protecting groups may effectively be removed by reductive cleavage of the derivative in the presence of sodium and liquid ammonia in an inert solvent such as an aromatic or aliphatic hydrocarbon under an inert atmosphere such as nitrogen at a temperature between −78° C. and 0° C.

Suitable methods for preparing the compounds of formula (I) by formation of the amido linkage include reacting a compound of formula (IV):

$$NH_2CH_2CN \qquad (VI)$$

with a carbonium ion of formula (VII):

$$E^{\oplus} \qquad (VII)$$

wherein E is as defined in formula (I) above. If desired the amino group in formula (VI) may be masked by a protecting group as defined in formula (V) above to provide a compound of formula (VIII):

$$ZCH_2CN \qquad (VIII)$$

wherein Z is Q as defined in formula (V) above. After formation of the amido linkage between a compound of formula (VIII) and a carbonium ion of formula (VII) the deprotection of the amino group to yield a compound of formula (I) may be carried out as described above.

The carbonium ion of formula (VII) may be conveniently generated under acidic conditions from the appropriate alcohol by protonation and subsequent dehydration; from the appropriate alkene by direct protonation of the carbon to carbon double bond or from the appropriate alkyl halide by heterolysis of the carbon-halogen bond. An acid catalyst is necessary for the reaction to occur and may be provided by a Lewis acid such as tin (IV) chloride or by a mineral acid such as sulphuric acid. The reaction may conveniently be effected in a polar solvent which includes chlorinated hydrocarbons such as chloroform, ethers such as di-n-butyl ether and organic acids such as glacial acetic acid or trifluoroacetic acid at a temperature in the range of −20° C. to 80° C.

The present invention also relates to compounds of formula (IX):

$$GCH_2CONHE \qquad (IX)$$

wherein E is as defined in formula (I), and G is selected from nitro, azido, $NHR^2$ and $N=R^3$;
wherein $R^2$ may be selected from formyl, halogenated alkanoyl of one to four carbon atoms, aralkyl, aralkoxycarbonyl, alkoxycarbonyl, arenesulphonyl, alkylarenesulphonyl, and trimethylsilyl; and $R^3$ may be selected from alkylidene, aralkylidene, and diacyl radicals of arene- or alkane-dicarboxylic acids. All compounds of formula (IX) are encompassed by formula (V) above and are all masked amino derivatives of compounds of formula (I). They may be deprotected to compounds of formula (I) as described above.

The compounds of formula (IX) may be synthesized by any known method for preparing compounds of analogous structure and particularly by formation of the amido linkage.

The compounds of formula (IX) wherein G is azido or aralkylamino may conveniently be prepared by reacting a compound of formula (IV) with sodium azide or with the appropriate aralkylamine in a polar solvent such as an alkanol at the reflux temperature of the reaction mixture.

Suitable methods for preparing the compounds of formula (IX) include reacting a compound of formula (X):

$$G'CH_2CN \qquad (X)$$

with a carbonium ion of formula (VII) wherein G' is selected from nitro, azido, $NHR^4$ and $N=R^5$;
wherein $R^4$ may be selected from formyl, halogenated alkanoyl, aralkyl, alkoxycarbonyl, arenesulphonyl and alkylarenesulphonyl; and $R^5$ may be selected from diacyl radicals derived from arene- or alkene-dicarboxylic acids. The reaction may be effected as described in the reaction of a compound of formula (VIII) with a carbonium ion of formula (VII) above.

The compounds of formula (IX) may also be prepared by reacting a compound of formula (XI):

$$G''CH_2COR^6 \qquad (XI)$$

wherein $R^6$ represents the free acid or a reactive acid derivative thereof selected from the acid halide, the acid anhydride, an ester or a thioester; G'' is an imido group derived from an arene- or an alkane-dicarboxylic acid, trimethylsilylamino, aralkoxycarbonylamino, alkylideneimino or aralkylideneimino; with an amine of formula:

$$NH_2E \qquad (XII)$$

wherein E is as defined in formula (I). The reaction may be carried out by standard techniques of peptide synthesis known in the art, conveniently in a polar solvent such as an alkanol or a chlorinated hydrocarbon in the presence of a molar equivalent to the concentration of a compound of formula (XI) of an acid acceptor, preferably a free amine, at a temperature in the range of −20° C. to 80° C. (See for example "Peptide Synthesis", Miklos Bodanszky and Miguel Ondetti, Interscience, 1966).

The compounds of formula (I) or acid addition salts thereof may be used in the treatment of prophylaxis of depression such as the normal grief reaction to adversity, especially associated with loss; neurotic or reactive depression associated with anxiety, somatic concern and tension; agitated depression; endogeneous or psychotic depression associated with emotional withdrawal, motor retardation, blunted affect, guilt feelings and conceptual disorganisation; bipolar depression where the compounds of formula (I) may be useful in the treatment of the acute episode and in continuous treatment to prevent lapses; involutional depression; senile depression and depression showing features of both neurotic and endogeneous depression associated with hostility and suspiciousness.

The optimum amount of a compound of formula (I) or an acid addition salt thereof (hereinafter referred to as the active ingredient) required for therapeutic effect will vary with the compound chosen, with the route of administration, and the nature and severity of the condition under treatment. In general a suitable dose of an active ingredient will lie in the range of 0.1 mg to 150 mg of base per kilogram bodyweight of the mammal to be treated, and the most preferred dosage being 1 mg/kg to 50 mg/kg of mammal bodyweight.

While it is possible for an active ingredient to be administered alone as the raw chemical, it is preferable to present it as a pharmaceutical formulation. Conveniently the active ingredient comprises from 5% to 95% by weight of the formulation and is preferably administered in unit dosage form to a mammal undergoing treatment. Conveniently unit doses of a formulation contain between 5 mg and 250 mg of the active ingredient.

The formulations, of the present invention when used for human medical use comprise an active ingredient together with one or more acceptable carriers therefor and optionally other therapeutic ingredients. The carrier(s) must be "acceptable" in the sense of being compatible with the other ingredients of the formulation and not deleterious to the recipient therefor.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets, tablets or lozenges each containing a predetermined amount of the active ingredient; as a powder or granules; or as a solution or a suspension in an aqueous liquid or non-aqueous liquid; or as an oil-in-water emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form which as a powder or granules, optionally mixed with a binder, lubricant, inert diluent, surface active or dispersing agent. Moulded tablets may be made by moulding in a suitable machine, a mixture of the powdered active ingredient and suitable carriers moistened with an inert liquid diluent.

Formulations for rectal administration may be presented as a suppository with the usual carriers such as cocoa butter.

Formulations suitable for parenteral administration conveniently comprise sterile aqueous preparations of the active ingredient which are preferably isotonic with the blood of the recipient.

In addition to the afore-mentioned ingredients, the formulations of this invention may include one or more additional ingredients such as diluents, buffers, flavouring agents, binders, surface active agents, thickeners, lubricants, preservatives and antioxidants.

It will be apparent from the foregoing that novel features of this invention include:

(a) Compounds of formula (I) and acid addition salts thereof;

(b) Methods of preparing such compounds of formula (I) and acid addition salts thereof;

(c) Pharmaceutical formulations containing a compound of formula (I) or an acid addition salt thereof;

(d) Methods of preparing such pharmaceutical formulations;

(e) A method of treating or preventing depression in a mammal comprising the administration to said mammal, including man, of an anti-depressant, effective, non-toxic amount of a compound of formula (I) or a pharmaceutically acceptable acid addition salt thereof; and (f) Compounds of formula (IX).

The following Examples are provided by way of an illustration of the present invention and should in no way be construed as constituting a limitation thereof.

All temperatures are indicated in degrees Celcius.

EXAMPLE 1—Preparation of 2-phthalimido-N-(1,1-dimethylhexyl)acetamide 1. 2-Methylheptan-2-ol (56.53 g.; 0.43 mole) and phthalimidoacetonitrile (80.27 g.; 0.43 mole) were dissolved in glacial acetic acid (220 ml.) and the solution warmed to about 60° C. with stirring. Concentrated sulphuric acid (59 ml.; 1.1 mole) was then added gradually; at first the temperature fell but as the addition proceeded a vigorous exothermal reaction took place, the temperature of the reaction was controlled at 70° C. by regulating the addition of the sulphuric acid and cooling as necessary. When the addition was complete the resulting dark brown solution was stirred for 1½ hours and then added dropwise to a mixture of ice and water. The precipitated solid was filtered off, pressed well, washed with fresh water and dried in vacuo. The residue was recrystallised from benzene with filtering, to afford 2-phthalimido-N-(1,1-dimethylhexyl)acetamide m.p. 142° C.

2. 2-Phthalimidoacetonitrile (3.72 g.-20 mmole) and stannic chloride (5.73 g.; 22 mmol) were dissolved in dry ethanol-free chloroform (15 ml.). The solution was stirred at −5° C. and a solution of 2-methylheptan-2-ol (2.60 g.; 20 mmol) in pure dry chloroform (5 ml.) was added at −5° C. over a period of 5 minutes. The mixture was stirred at −5° C. for 10 minutes, at which point a precipitate separated from the clear reaction mixture. After a further 10 minutes the reaction mixture was poured into water with vigorous stirring. The aqueous layer was removed and reextracted with chloroform (2×30 ml.) and the combined extracts dried over magnesium sulphate, filtered and evaporated. The residue was recrystallised from benzene to give pure 2-phthalimide-N-(1,1-dimethylhexyl)acetamide m.p. 146°–148° C.

EXAMPLE 2—Preparation of 2-Amino-N-(1,1-dimethylhexyl)acetamide

1. Hydrazine hydrate (1.44 g.; 0.029 mol) was added to N-(1,1-dimethylhexyl)-2-phthalamidoacetamide (9.0 g.; 0.028 mol) in ethanol (60 ml.). The mixture was then heated under reflux for 0.5 hours, cooled to room temperature and evaporated, first at ca. 25° C. (Buchi) and then at room temperature (max. water-pump vacuum, then oil-pump vacuum (0.5 mm/10 min.)). The resultant syrupy mixture was treated with dilute sulphuric acid (0.4 N, 100 ml.) and chilled to 10° C. The mixture was cooled to ca. 0°-5° C., filtered, and the precipitate washed with water (ca. 2×50 ml.). The combined filtrate was basified with sodium hydroxide solution (5 N; 20 ml.), and then extracted with dichloromethane (3×50 ml.). The combined organic phase was washed with water, and dried (sodium sulphate). After removal of the solvent as usual, followed by drying in vacuo (0.5 mm/r.t./10 min.) 2-amino-N-(1,1-dimethylhexyl)acetamide remained as a clear slightly coloured oil. T.l.c. (silica; ethyl acetate), one spot Rf. ca. 0.6.

2. 2-phthalimido-N-(1,1-dimethylhexyl)acetamide (88.95; g.; 0.28 mole) was suspended in ethanol (1180 ml.), hydrazine hydrate (27 ml.; 0.56 mole) was added, the mixture stirred at reflux for 1 hour and then cooled. The separated solid was filtered off and washed with fresh ethanol. The combined filtrate and washings were evaporated in vacuo to give an oil; this was extracted with petroleum ether (b.p. 60°-80° C.), the solution separated from the insoluble part and evaporated. The residue was distilled in vacuo b.p. 86°-92° C./0.1 mm. to give pure 2-amino-N-(,1-dimethylhexyl)acetamide as a colourless oil, b.p. 86°-92° C./0.1 mm.

EXAMPLE 3—Preparation of 2-Amino-N-(1-methylcyclohexyl)acetamide

1. A solution of phthalimidoacetonitrile (9.3 g.) and 1-methylcyclohexanol (6.28 g.) in glacial acetic acid (30 ml.) was warmed to 50° C. and concentrated sulphuric acid (12 ml.) slowly added. A vigorous reaction ensued and the temperature of the mixture was kept between 75° C. and 80° C. by cooling and manipulating the rate of addition of sulphuric acid. The final mixture was maintained at 50°-60° C. for 30 minutes, cooled and poured on to a mixture of ice and water. A crystalline solid separated. This was collected by filtration, washed with water and dried by pressing on a porous plate. The final residue was extracted twice with hot benzene and the filtered solution kept at 5° C. The resulting N-(1-methylcyclohexyl)-2-phthalimidoacetamide was filtered off and dried in vacuo, m.p. 194.7° C. Addition of light petroleum (b.p. 40°-60° C.) to the filtrate afforded a second crop, m.p. 194.2° C.

2. This phthalimide (8.0 g.; 0.0266 mole) was dissolved in hot ethanol (120 ml.) and the resulting solution stirred whilst hydrazine hydrate (2.66 g; 0.0532 mole) was added. After some 15 minutes at reflux a colourless crystalline solid separated to produce a semi-solid mass. After a further 30 minutes the mixture was cooled and filtered. The thixotropic residue was pressed well and washed with fresh ethanol. The combined filtrate and washings was evaporated in vacuo to give 2-amino-N-(1-methylcyclohexyl)acetamide as a colourless oil; its hydrogen oxalate was crystallised from hot water as colourless plates, m.p. 192°-193° C.

EXAMPLE 4—Preparation of 2-Amino-N-(1-methylcycloheptyl)acetamide

1. By processes similar to those described in Examples 1, 2 and 3, phthalimidoacetonitrile (27.9 g.) was caused to react with 1-methylcycloheptan-1-ol (24 g.) in glacial acetic acid solution (90 ml.) at 50° C. by the addition of concentrated sulphuric acid (0 ml.). After the initial vigorous reaction, a further 6 ml. of sulphuric acid was added. After 2 hours the resulting N-(1-methylcycloheptyl)-2-phthalimidoacetamide was isolated by pouring into water; it was collected, washed and dried before crystallisation from benzene; it was obtained as a colourless crystalline solid, m.p. 190° C.

2. This product (18.6 g.) was reacted with hydrazine hydrate (6.4 g.) still under the conditions employed in Examples 1, 2 and 3. The resulting 2-amino-N-(1-methylcycloheptyl)acetamide was purified as its hydrogen oxalate which was recrystallized from hot water, m.p. 177° C. The hydrochloride was recrystallized from a mixture of isopropanol, ether and light petroleum, m.p. 152° C.

EXAMPLE 5—Preparation of 2-Amino-N-(1,1-dimethylpentyl)acetamide 1. 2-Phthalimidoacetonitrile (14.4 g.) was reacted with 2-methylhexan-2-ol (7.5 g.) in glacial acetic acid by the addition of concentrated sulphuric acid (15 ml.) according to the process described in Example 1. The resulting N-(1,1-dimethylpentyl)-2-phthalimidoacetamide was recrystallised from benzene, m.p. 189°-190° C. It was then reacted with hydrazine hydrate (2.8 g.) in ethanol (100 ml.) as in Example 2 and the product purified as its hydrogen oxalate; 2-amino-N-(1,1-dimethylpentyl)acetamide hydrogen oxalate.

EXAMPLE 6—Preparation of 2-Amino-N-(1,1,3-trimethylhexyl)acetamide hydrogen succinate 2-Phthalimidoacetonitrile (3.85 g) was dissolved in glacial acetic acid at 70° and 2,4-dimethylheptan-2-ol (3 g) was added; followed dropwise by conc. sulphuric acid (2.8 ml) the temperature being maintained between 65° and 70°. The final mixture was stirred for 15 minutes and then added slowly to ice cold water (150 ml). The resulting solid was collected, washed with water and dried in vacuo. It was dissolved in hot benzene, a little insoluble material filtered off and light petroleum (b.p. 40°-60° ) added to give 2-phthalimido-N-(1,1,3-trimethylhexyl)acetamide as a colourless solid, m.p. 131.6°.

A mixture of this solid (2.37 g), ethanol (10 ml) and hydrazine hydrate (0.35 g) was heated to reflux for 1 hour. After cooling, the precipitated solid was filtered off and the filtrate evaporated in vacuo. The residue was extracted with light petroleum (b.p. 60°-80° ) (25 ml), the insoluble portion being rejected. Evaporation of the petroleum solution afforded a mobile oil (1.33 g) which was reacted with succinic acid (0.78 g) in hot isopropanol. Addition of light petroleum (b.p. 60°-80°) to the resulting clear solution produced a crystalline solid which was filtered off and recrystallized from ethyl acetate to give 2-amino-N-(1,1,3-trimethylhexyl)acetamide hydrogen succinate, m.p. 101.8°.

EXAMPLE 7—Preparation of 2-Amino-N-(1,1-dimethylheptyl)acetamide

A suspension of 2-phthalimidoacetonitrile (11.2 g) and 2-methyloctan-2-ol (8.65 g) in glacial acetic acid was stirred and heated to 60°. Conc. sulphuric acid (11.5 ml) was then added dropwise and the temperature controlled at about 70° by external cooling. The addition was completed in about 15 minutes; the mixture was stirred for a further 5 minutes and then poured into ice/water mixture (150 ml). The resulting 2-phthalimido-N-(1,1-dimethylheptyl)acetamide was dried in vacuo and recrystallized from benzene, m.p. 146.9–147.2°.

A mixture of this solid (15.55 g), ethanol (55 ml) and hydrazine hydrate (2.36 g) was heated to reflux for 90 minutes. After cooling, the separated solid was filtered off and the filtrate evaporated in vacuo to give an oil. This was extracted with light pretroleum (b.p. 40°–60°), the insoluble material removed by filtration and the filtrate evaporated. The residual 2-amino-N-(1,1-dimethylheptyl)acetamide was distilled in vacuo, b.p. 88°–89°/0.025 mm.

This base was reacted with excess fumaric acid in ethanol solution and the resulting hydrogen fumarate precipitated with ether. It was recrystallized from hot water, m.p. 155.5°.

EXAMPLE 8—Preparation of N-(1-Methylhexyl)-2-phthalimidoacetamide

1. A solution of 2-phthalimidoacetyl chloride (12.3 g; 55 mmol) in dry ethanol-free chloroform (20 ml) was added dropwise to a mixture of 2-aminoheptane (5.78 g; 50 mmol) and potassium carbonate (13.82 g; 100 mmol) in the same solvent (30 ml), over 15 minutes under positive nitrogen pressure. During the addition the temperature was maintained below 30°. The mixture was then heated under reflux (1 hour), cooled, and poured into water (200 ml). The organic phase was separated and the aqueous phase extracted with more chloroform (2×50 ml). The combined chloroform extracts were washed with citric acid solution (5%; 2×50 ml), dried (sodium sulphate), and the crude product purified by column chromatography (silica column; 40 cm.×7 cm.; chloroform, then 10% ethylacetate on chloroform), m.p. 147°–149.5°. T.l.c. (silica; ethyl acetate): 1 spot, Rf. 0.7. Found: C, 67.68; H, 7.30; N, 9.17%. $C_{17}H_{22}N_2O_3$ requires C, 67.53; H, 7.33; N, 9.26%.

2. Preparation of 2-Amino-N-(1-methylhexyl)acetamide

A solution of hydrazine hydrate (1.14 g; 22.8 mmol) and N-(1-methylhexyl)-2-phthalimidoacetamide (6.9 g; 22.8 mmol) in ethanol (50 ml) was heated under reflux for 1 hour. It was then cooled to room temperature and evaporated in vacuo (Buchi, r.t.; then oil-pump, 0.5 mm/r.t./10 min.). The resultant semi-solid mixture was treated with dilute sulphuric acid (0.5 N; 85 ml) precooled to 5°. The mixture was cooled to 0°, filtered and the precipitate mixed with more of the acid (2 N; 3×20 ml). The filtrate was kept in the refrigerator overnight and then filtered once more. After basification with sodium hydroxide solution (5 N; 40 ml), the mixture was extracted with dichloromethane (3×50 ml), the extracts dried (sodium sulphate) and evaporated in vacuo. The resultant oil was dried at 0.5 mm./r.t./0.5 h. T.l.c. (silica; chloroform:methanol: 3:2): 1 major spot, Rf. ca 0.5. I.v. and n.m.r. spectra were consistent with the structure. The product was purified as its hydrogen succinate.

3. Preparation of 2-Amino-N-(1-methylhexyl)acetamide hydrogen succinate

Succinic acid (1.75 g; 1 mol. equiv.) was dissolved in the minimum quantity of hot ethanol (20 ml). 2-Amino-N-(1-methylhexyl)acetamide (2.54 g) was added and washed in with ether (ca 10 ml). The mixture was diluted with ether (50 ml), whereupon the product began to crystallise out. After being cooled in the refrigerator, the product was filtered off and dried in vacuo (0.2 mm/r.t./2 h.) m.p. 105°. T.l.c. (silica; $CHCl_3$: MeOH: 3:2; ammonia): 1 spot, Rf ca.0.75 ($I_2$), apart from succinic acid at origin. Found: C, 53.21%, H, 9.05%; N, 9.92%. $C_{13}H_{26}N_2O_5$ requires C, 53.79%; H, 9.03%; N, 9.65%.

$CHCl_3$: chloroform MeOH: methanol
$I_2$: iodine

EXAMPLE 9—Preparation of (±)-2-Amino-1-cyclohexylpropane

1. A solution of (±)-2-Amino-1-phenylpropane (12.0 g) in water (125 ml) containing glacial acetic acid (10 ml) was hydrogenated over $RuO_2.H_2O$ (0.5 g) at 150 atm. at a temperature of 90° for 2.5 hours. After cooling, the solution was filtered abd basified with 0.880 ammonia solution. The liberated base was extracted into ether (3×200 ml) and the combined extracts dried over sodium sulphate, filtered, and evaporated to dryness giving a colourless oil. The product was homogeneous by t.l.c. (HCl-MeOH, 1:99; one spot Rf 0.65).

$RuO_2.H_2O$: ruthenium (IV) oxide mono-hydrate

2. Preparation of (±)-N-(2-Cyclohexyl)-1-methylethyl)-2-phthalimidoacetamide

To a soluton of (±)-2-amino-1-cyclohexylpropane (7.6 g, 53.9 mmol) and triethylamine (6.0 g, 59.3 mmol) in dry ethanol free chloroform (50 ml), was added 2-phthalimidoacetyl chloride (11.35 g, 59.3 mmol) over 20 minutes.

The temperature of the reaction mixture was maintained below 10° with external cooling. When the addition was complete, te reaction mixture was stirred at room temperature for 1 hour. The homogeneous solution was then extracted with water (2×200 ml), 5% citric acid solution (2×100 ml) and 5% sodium hydrogen carbonate solution (2×100 ml). The chloroform solution was dried over sodium sulphate, filtered, and evaporated to dryness giving a colourless solid which was crystallised from ethanol-water (8:3) to give colourless needles, m.p. 163°–165° C.

Found: C, 69.22; H, 7.31; N, 8.38. $C_{19}H_{24}N_2O_3$ requires: C, 69.51; H, 7.32; N. 8.54.

3. Preparation of (±)-2-Amino-N-(2-cyclohexyl)-1-methylethyl)acetamide hydrogen fumarate To a suspension of (±)-N-(2-cyclohexyl-1-methylethyl)-2-phthalimidoacetamide (12.0 g, 36.7 mmol) in ethanol (180 ml) was added hydrazine hydrate (2.05 g, 40.3 mmol) and the mixture heated under reflux for 1.5 hours. After cooling and standing at 0° for 24 hours, the slurry was filtered and the residue washed with petrol (40°–60°). The combined filtrates were evaporated to dryness and the oily residue triturated with petrol (3×100 ml). The combined extracts were evaporated to dryness to give a colourless oil. The oil was dissolved in ether (50 ml) and the solution added to a warm solution of fumaric acid (2.7 g) in ethanol (50 ml). On standing, a colourless solid was deposited, m.p. 132°–134° C.

Found: C, 57.15; H, 8.34; N, 8.97. $C_{11}H_{22}N_2O.C_4H_4O_4$ requires: C, 57.33; N, 8.28; N, 8.92.

EXAMPLE 11—Preparation of Ethyl cyclopentylacetate

1. Hydrogen chloride was passed into a solution of cyclopentylacetic acid (25 g) in ethanol (200 ml) until no further increase in temperature was observed. The solution was poured onto crushed ice (800 g) and the mixture extracted with ether (4×100 ml). The combined ether extracts were washed with water (2×200 ml), 5% sodium carbonate (2×200 ml) and then dried over magnesium sulphate. Filtration and evaporation to dryness gave a colourless oil.

2. Preparation of 2-Cyclopentyl-1,1-dimethyl ethanol

A solution of methyl magnesium iodide was prepared by treating a suspension of magnesium (12.7 g; 0.521 mol) in ether (400 ml) with iodomethane (74.1 g, 0.521 mol) in ether (200 ml) employing the usual conditions. The methyl magnesium iodide solution was cooled to 0° and a solution of ethyl cyclopentylacetate (27.3 g, 0.174 mol) in ether (100 ml) run in over 30 minutes keeping the temperature of the reaction mixture below 0° throughout. When the addition was complete, the reaction mixture was stirred at 25° for 1 hour, heated under reflux for 1 hour, cooled to 0° and treated slowly with a solution of ammonium chloride (46 g) in water (250 ml). The phases were separated and the aqueous layer was extracted with ether (3×100 ml). The combined ether extracts were dried over sodium carbonate, filtered and evaporated to dryness to give an almost colourless oil.

3. Preparation of 2-Phthalimido-N-(1,1-dimethyl-2-cyclopentylethyl)acetamide

To a solution of 2-phthalimidoacetonitrile (11.2 g, 60 mmol) in trifluoroacetic acid (25 ml) at 0°–5° was added 2-cyclopentyl-1,1-dimethylethanol (8.52 g, 60 mmol) over 20 minutes. The reaction mixture was then stirred at 25° for 2 hours, poured into stirred water (200 ml), and the precipitated solid collected. The crude product was crystallized from ethanol-water (1:1) giving colourless needles m.p. 159°–160°. Found: C, 69.66; H, 7.18; N, 8.22. $C_{19}H_{24}N_2O_3$ requires C, 69.51; H, 7.32; N, 8.53.

4. Preparation of 2-Amino-N-(1,1-dimethyl-2-cyclopentylethyl)acetamide hydrogen fumarate monoethanolate A suspension of 2-phthalimido-N-(1,1-dimethyl-2-cyclopentylethyl)acetamide (15.8 g, 48.2 mmol) in ethanol (50 ml) was treated with hydrazine hydrate (2.65 g, 53.0 mmol) and the mixture heated under reflux for 1 hour. After cooling and allowing to stand at 0° for 24 hours, the slurry was filtered and the residue washed with petrol (40°–60°) (2×25 ml). The combined filtrates were evaporated to dryness and the colourless oily residue triturated with petrol (40°–60°, 100 ml). The insoluble material was filtered off and the filtrate evaporated to dryness giving a colourless oil. The oil was dissolved in ethanol (30 ml) and treated with a hot solution of fumaric acid (5.9 g) in ethanol (80 ml). On diluting with ether (100 ml) and cooling, colourless plates were deposited, m.p. 159°–160°. Found: C, 56.75; H, 8.78; N, 7.89; $C_{11}H_{22}N_2O.C_4H_4O_4C_2H_5OH$ requires C, 56.67; H, 8.89; N, 7.78.

EXAMPLE 12—Preparation of 2-Amino-N-(1,1,5-trimethylhexyl)acetamide

A suspension of phthalimidoacetonitrile (6.01 g, 0.03 mole) in glacial acetic acid (16 ml) was heated to 60° C. with stirring; 2,6-dimethylheptan-2-ol (4.64 g, 0.03 mole) was then added followed dropwise by concentrated sulphuric acid (4.4 ml, 0.08 mole). The temperature rapidly rose to 20° and was controlled at this temperature during the addition. When the addition was complete the solution was stirred for 5 minutes and then added slowly to a mixture of ice and water (350 g). The precipitated solid was filtered off, washed thoroughly with water and dried in vacuo. The product was recrystallised from benzene with filtering to afford 2-phthalimido-N-(1,1,5-trimethylhexyl)acetamide, m.p. 162°–163°.

This product (8.68 g, 0.026 mole) was heated to reflux in ethanol (30 ml) and hydrazine hydrate (1.3 g, 0.026 mole) added, after which heating was continued for 30 minutes. After cooling the separated solid was filtered off and washed with a little fresh ethanol. The combined filtrate and washings were evaporated in vacuo to give an oil; this was extracted with petroleum ether (b.p. 40°–60°), the solution separated from the insoluble part and evaporated. The residue was distilled in vacuo to give pure 2-amino-N-(1,1,5-trimethylhexyl)acetamide, b.p. 92°/0.15 mm. The hydrogen succinate was prepared by addition of the base to a molar equivalent of succinic acid dissolved in isopropanol and precipitating the salt by addition of a large volume of petroleum ether (b.p. 40°–60°); it was recrystallized from ethyl acetate, m.p. 113.2°.

EXAMPLE 15—Preparation of 2-Chloro-N-(1,1-dimethylhexyl)acetamide

1. A solution of chloroacetonitrile (15.1 g., 0.2 mol) and 2-methylheptan-2-ol (26.0 g., 0.2 mol) in acetic acid (120 ml) was treated with concentrated sulphuric acid (24 ml) with the temperature maintained at 40°–50° C. After stirring for ½ hour the mixture was poured into ice-water (500 ml) and extracted with ether (3×400 ml). The combined extracts were washed with aqueous sodium carbonate until neutral and then evaporated to give 2-chloro-N-(1,1-dimethylhexyl)acetamide as a colourless solid m.p. 36°–37° C., b.p. 60°–62° C. at 0.01 mm Hg.

2. A solution of 2-methylhept-2-ylamine (2.58 g, 20 m mol) and N,N-diisopropylethylamine (3.87 g, 30 m mol) in chloroform (20 ml) was treated with chloroacetylchloride (1.60 ml, 20 m mol) with the temperature held below 15° C. The resulting solution was washed with N hydrochloric acid (2×30 ml), dried over magnesium sulphate and evaporated to give a brown solid (3.5 g). Distillation afforded 2-chloro-N-(1,1-dimethylhexyl)acetamide as a colourless solid m.p. 36°–36.5° C. 2-Methylhept-2-ylamine was prepared as described by K. E. Hamlin and N. Freifelder in J.A.C.S., 1953, 75, 369.

EXAMPLE 16—Ammonolysis of 2-chloro-N-(1,1-dimethylhexyl)acetamide

A suspension of 2-Chloro-N-(1,1-dimethylhexyl)acetamide (2.5 g, 12 m mol) in a mixture of water (50 ml) and ethanol (50 ml) was saturated in ammonia in the cold and held at room temperature for two days with the occasional passage of ammonia. The mixture was evaporated to a gum which was partially dried by azeotroping with ethanol then 40–60 petrol. The residue was dissolved in chloroform (50 ml) and stirred with sodium carbonate (2 g) and water (10 ml) for ½ hour. The organic phase was then separated, dried over magnesium sulphate, evaporated to a yellow oil and distilled to give 2-amino-N-(1,1-dimethylhexyl)acetamide as a colourless oil, b.p. 109°–113° C. at 0.4 mm Hg.

EXAMPLE 17—Preparation and hydrogenation of 2-azido-N-(1,1-dimethylhexyl)acetamide A solution of sodium azide (6.7 g, 103 m mol) in water (56 ml) and methanol (104 ml) was treated with 2-chloro-N-(1,1-dimethylhexyl)acetamide (16.5 g, 80 m mol) and the mixture was refluxed for 5 hours. After cooling, the mixture was extracted with 40-60 petrol (3×200 ml), the extracts were dried over magnesium sulphate and evaporated under reduced pressure to give crude 2-azido-N-(1,1-dimethylhexyl)acetamide as a pale yellow oil. This oil was dissolved in methanol (200 ml) and hydrogenated over 10% palladium on charcoal (3.2 g) at atmospheric pressure and room temperature for 24 hours. The mixture was filtered and the filtrate evaporated to give a crude oil (13.6 g) which was distilled to give 2-amino-N-(1,1-dimethylhexyl)acetamide as a colourless oil, b.p. 88°-90° C. at 0.05 mm Hg.

EXAMPLE 18—Preparation of 2-Benzylamino-N-(1,1-dimethylhexyl)acetamide

A solution of benzylamine (21.4 g, 0.2 mol) and 2-chloro-N-(1,1-dimethylhexyl)acetamide (20.6 g, 0.1 mol) in benzene (100 ml) was held at room temperature for five days then refluxed for 24 hours. The mixture was filtered and the filtrate was evaporated then distilled under reduced pressure to give 2-benzylamino-N-(1,1-dimethylhexyl)acetamide as a pale yellow oil, b.p. 153°-156° C. at 0.05 mm Hg.

EXAMPLE 19—Hydrogenation of 2-benzylamino-N-(1,1-dimethylhexyl)acetamide

A solution of 2-benzylamino-N-(1,1-dimethylhexyl)acetamide (15.8 g, 57 m mol) in acetic acid (160 ml) was hydrogenated over 10% palladium on charcoal (3.16 g) for 2 hours at atmospheric pressure and 80° C. The mixture was filtered and the filtrate evaporated to a viscous liquid (15 g). This was dissolved in water (40 ml), basified with 10 N sodium hydroxide solution and extracted with ether (3×50 ml). The combined extracts were dried over magnesium sulphate then evaporated and distilled to give 2-amino-N-(1,1-dimethylhexyl)acetamide as a colourless oil, b.p. 92°-94° C. at 0.1 mm Hg.

EXAMPLE 20—Preparation of 2-Amino-N-(1,1-dimethylhexyl)acetamide

1. A mixture of aminoacetonitrile bisulphate (15.4 g, 0.1 mol) and 2-methylheptan-2-ol (13.0 g, 0.1 mol) in acetic acid (60 ml) was treated with concentrated sulphuric acid (12 ml) with the temperature held at 40°-45° C. After stirring for 1 hour the mixture was poured into ice-water (300 ml) and washed with ether (2×200 ml). The aqueous phase was basified with 10 N sodium hydroxide solution, extracted with ether (3×200 ml) and the combined extracts were dried over magnesium sulphate then distilled to give 2-amino-N-(1,1-dimethylhexyl)acetamide as a colourless oil, b.p. 104°-110° C. at 0.2 mm Hg.

2. A mixture of aminoacetonitrile hydrochloride (9.25 g, 0.1 mol) and 2-methylheptan-2-ol (13.0 g, 0.1 mol) in acetic acid (60 ml) was treated with concentrated sulphuric acid (12 ml) with the temperature held at 25°-30° C. After stirring for 2 hours the mixture was poured into ice-water (300 ml) and washed with ether (2×200 ml). The aqueous phase was basified with 10 N sodium hydroxide solution, extracted with ether (3×200 ml) and the combined extracts were dried over magnesium sulphate then evaporated to give 2-amino-N-(1,1-dimethylhexyl)acetamide.

EXAMPLE 21—Preparation of 2-Trifluoroacetamidoacetonitrile

A vigorously stirred suspension of very finely powdered aminoacetonitrile bisulphate (38.0 g.; 0.25 mole) in absolute ethanol (100 ml) was saturated with gaseous ammonia and the temperature was maintained below 10° C. with external cooling. The slurry was cooled to −10° C., filtered, and the residue washed with cold (−10°) absolute ethanol (2×50 ml). The combined filtrates were evaporated to dryness at 35°-40° C. under reduced pressure (water pump) and the colourless residual oil (13.0 g) dissolved in ethyl trifluoroacetate (100 ml). After heating at reflux for 2 hours, the excess ester was distilled off and the pale tan oil cooled to give pale tan needles, m.p. 39°-40° C.

EXAMPLE 22—Preparation of 2-Trifluoroacetamido-N-(1,1-dimethylhexyl)acetamide To a solution of 2-trifluoroacetamidoacetonitrile (5.36 g.; 0.04 mole) in trifluoroacetic acid (20 ml) at 0° C. was added 2-methylheptan-2-ol (5.2 g.; 0.04 mole) over 10 minutes. When the addition was complete, the reaction mixture was stirred at room temperature for 2 hours and then poured into cold water (100 ml). The precipitated solid was collected by filtration and crystallisation from ethanol-water gave almost colourless needles, m.p. 68°-69° C.

Found: C, 51.17; H, 7.38; N, 9.78%. $C_{12}H_{21}F_3N_2O_2$ requires C, 51.06; H, 7.45; N, 9.93%.

EXAMPLE 23—Preparation of 2-Amino-N-(1,1-dimethylhexyl)acetamide hydrogen fumarate A solution of 2-Trifluoroacetamido-N-(1,1-dimethylhexyl)acetamide (2.0 g) in ethanol (20 ml) was treated with 0.880 ammonia (2.0 ml) and the mixture was warmed to 50°. After 2 hours, the reaction mixture was evaporated to dryness and the residue extracted with ether (2×50 ml). The combined extracts were dried over $Na_2SO_4$, filtered and evaporated to dryness to give a colourless oil which was converted to the hydrogen fumarate salt, m.p. 158°-161° C. Found: C, 55.66; H, 8.57; N, 9.14%. $C_{10}H_{22}N_2O \cdot C_4H_4O_4$ requires C, 55.63; H, 8.61; N, 9.27%.

EXAMPLE 24—Preparation of 2-Amino-N-(1,1-dimethylhexyl)acetamide hydrogen fumarate To a solution of 2-methylheptan-2-ol (6.50 g.; 0.05 mole) in trifluoroacetic acid (20 ml) at −5° C. was added powdered methyleneaminoacetonitrile (3.40 g.; 0.05 mole) over 10 minutes. The slurry was allowed to warm to 10° C. and stirred until homogeneous (2 hours). After an additional 2 hours at 10° C., the reaction mixture was poured into water (100 ml) and the neutral material extracted with ether. The acid solution was basified with ammonia (pH 9-10) and the liberated base extracted into ether (3×80 ml). The combined extracts were dried over $Na_2SO_4$, filtered, and evaporated to dryness to give a colourless oil which was converted to the hydrogen fumarate salt, m.p. 156°-158° C.

Found: C, 55.91%, H, 8.93; N, 9.08%. $C_{10}H_{22}N_2O \cdot C_4H_4O_4$ requires C, 55.63; H, 8.61; N, 9.27%.

$Na_2SO_4$:sodium sulphate

EXAMPLE 25—Preparation of 2-Formamidoacetonitrile

A vigorously stirred suspension of very finely powdered aminoacetonitrile bisulphate (77.0 g, 0.50 mol) in absolute ethanol (200 ml) was treated with gaseous ammonia until saturated, the temperature being maintained below 20° C. with external cooling. The slurry was then cooled to −10° C., filtered, and the residue washed with cold (−10° C.) absolute ethanol (2×100 ml). The combined filtrates were evaporated to dryness at 40° C. under reduced pressure (water pump). The residue (25.6 g) of aminoacetonitrile was dissolved in ethyl formate (200 ml) and the solution refluxed for 1 hour. The excess ester was evaporated in vacuo and the dark brown oil distilled under reduced pressure (120°–124° C./0.10–0.15 mm) to give 2-formamidoacetonitrile as a colourless oil.

EXAMPLE 26—Preparation of 2-Amino-N-(1,1-dimethylhexyl)acetamide hydrogen fumarate A mixture of 2-methylheptan-2-ol (4.55 g.; 35 m.mol) and 2-formamidoacetonitrile (2.94 g.; 35 m.mol) was added dropwise over 10 minutes to stirred trifluoroacetic acid (15 ml) at 10° C. The temperature of the reaction mixture was maintained at 10° C. throughout the addition and then allowed to rise to room temperature over 30 minutes. After stirring for an additional 1 hour, the reaction mixture was evaporated to dryness in vacuo (water pump) at 80° C. and the colourless residual oil dissolved in ethanol (70 ml). The solution was then treated with concentrated hydrochloric acid (7.0 ml) and the mixture refluxed for 1 hour and then evaporated to dryness. The colourless gum was dissolved in methanol (30 ml) and the solution treated with ether (30 ml). After stirring for 30 minutes, the precipitated solid was filtered off, the filtrate evaporated to dryness and the residual gum dissolved in water (50 ml). The colourless solution was basified with concentrated ammonia (pH 10) and the liberated base extracted with ether (4×50 ml). The combined extracts were dried over sodium sulphate, filtered and evaporated to dryness giving a colourless oil (5.20 g). The oil was dissolved in ethanol (10 ml) and treated with a solution of fumaric acid (3.6 g) in hot ethanol (30 ml) followed by ether (60 ml). On standing colourless plates were deposited. The product was filtered off, washed with ether and sucked dry to give pure 2-amino-N-(1,1-dimethylhexyl)acetamide hydrogen fumarate, m.p. 155–157.

Anal. Found: C, 55.60; H, 8.37; N, 9.17%. $C_{10}H_{22}N_2O.C_4H_4O_4$ C, 55.63; H, 8.61; N, 9.27%.

EXAMPLE 27—Preparation of a mixture of 2-Methylhept-1-ene and 2-methylhept-2-ene 1. A mixture of pulverised, fused potassium hydrogen sulphate (38 g) and 2-methylheptan-2-ol (20 g) was heated under reflux for 3 hours (internal temperature ca 120° C.). The mixture was then allowed to cool to room temperature and the liquid portion carefully removed with a dropper, dried over sodium sulphate and distilled, the fraction b.p. 120°–124° being collected. G.l.c. indicated the absence of starting alcohol. I.r. and n.m.r. data were consistent with the product being a mixture of 2-methylhept-1-ene and 2-methylhept-2-ene and n.m.r. indicated the ratio of isomers was 1:1.1.

2. Preparation of 2-Amino-N-(1,1-dimethylhexyl)acetamide

A mixture (1:1.1) of 2-methylhept-1-ene and 2-methylhept-2-ene (4.0 g) was added to a suspension of aminoacetonitrile bisulphate (5.5 g; 1 mol equiv.) in acetic acid (22 ml). The resultant mixture was warmed to 40°. Conc. sulphuric acid (4.5 ml) was then added over 10 minutes with stirring, so that the temperature did not rise above 70°. The mixture was left for 1 hour and then poured into ice-water (200 g). The aqueous phase was washed with ether (2×100 ml), basified with 10 N sodium hydroxide solution (100 ml) (pH 14), and extracted with ether (3×100 ml). The combined ether extracts were washed with water (50 ml), dried, and evaporated in vacuo (Buchi; 20°) to give the product as a yellow oil, which was dried at 0.2 mm/0.5 h/r.t. By t.l.c., i.r. and n.m.r. this product was identical with 2-amino-N-(1,1-dimethylhexyl)acetamide prepared from 2-methylheptan-2-ol.

EXAMPLE 28—Preparation of 2-Amino-N-(1,1-dimethylhexyl)acetamide hydrogen succinate Succinic acid (0.70 g; 1.2 mol. equiv.) was dissolved in the minimum quantity of hot ethanol (10 ml). 2-Amino-N-(1,1-dimethylhexyl)acetamide (0.92 g) was added to the hot solution, with shaking, and was rinsed in with ether (10 ml). The mixture was then diluted with more ether (240 ml). After the mixture had stood overnight in the refringerator, the product was filtered off and dried in vacuo, m.p. 107.5°–109° C. T.l.c. (silica; methanol: $CHCl_3$; 2:3; ammonia): 1 spot, Rf, ca. 0.65, apart from spot corresponding to succinic acid. Found: C, 55.13; H, 9.46; N, 9.27%. $C_{14}H_{28}N_2O_5$ requires C, 55.24; H, 9.27; N, 9.20%.

$CHCl_3$:chloroform

EXAMPLE 29—Preparation of 2-Amino-N-(1,1-dimethylhexyl)acetamide hydrogen fumarate A solution of fumaric acid (12.6 g) in cold methanol (585 mls) was stirred and 2-amino-N-(1,1-dimethylhexyl)acetamide (18.47 g) added to give a clear solution which rapidly deposited a crystalline solid. After standing at 0° C. for 4 hours this solid was filtered off, washed with ethanol and dried in vacuo, m.p. 154° C.

EXAMPLE 30

The following salts were prepared by reacting a solution of the respective acid in isopropanol with a solution of pure 2-amino-N-(1,1-dimethylhexyl)acetamide base in the same. The crystals were filtered and recrystallized from hot water.

hydrogen oxalate: m.p. 175°–178° C.
hydrogen maleate: m.p. 125°–126° C.
neutral sulphate: m.p. 169°–170° C.
p-toluene sulphonate: m.p. 151° C. and
dihydrogen phosphate m.p. 136° C. (d).

The hydrochloride was a low melting point solid.

EXAMPLE 31—Preparation of 2-Amino-N-(1,1-dimethylhexyl)acetamide hydrogen tartrate 2-Amino-N-(1,1-dimethylhexyl)acetamide (5 g) was added to a solution of tartaric acid (4.03 g) in methanol (50 ml). The solution was concentrated to dryness on a rotary evaporator and yielded a white solid, m.p. 150.5° C.

EXAMPLE 32

The following salts were prepared by dissolving the appropriate acid in ethyl acetate, adding pure 2-amino-N-(1,1-dimethylhexyl)acetamide, filtering the crystals and finally washing with ethyl acetate:

formate: m.p. 91.5° C.
citrate: m.p. 120°–130° C.
benzene sulphonate: melting point 156°–157° C.

EXAMPLE 33

The following salts were prepared by dissolving the appropriate acid in ether, adding pure 2-amino-N-(1,1-dimethylhexyl acetamide), filtering the crystals and finally washing with a little more ether.

benzoate: m.p. 106° C.
hydrogen malonate: m.p. 125.4° C.
and methane sulphonate: m.p. 142°–143° C.

EXAMPLE 34

Nitric acid (2.43 g of a 70% aqueous solution) was mixed with ether (30 ml) and stirred while 5 g. of pure liquid 2-amino-N-(1,1-dimethylhexyl)acetamide was added dropwise with external cooling.

The product, 2-amino-N-(1,1-dimethylhexyl)acetamide nitrate separated out as white crystals, m.p. 118° C.

EXAMPLE 35

2-Amino-N-(1,1-dimethylhexyl)acetamide (5 g) was dissolved in ether (25 ml) and glacial acetic acid (1.61 g) added. Petroleum distillate (b.p. 40°–60° C.) was added whereupon an oil separated. The mixture was cooled and the resulting solid filtered off yielding 2-amino-N-(1,1-dimethylhexyl)acetamide acetate, m.p. 64° C.

EXAMPLE 36—Preparation of 2-Amino-N-(1,1-dimethylhexyl)acetamide naphthalene-2-sulphonate The sodium salt of naphthalene-2-sulphonic acid (6.22 g) was dissolved in water (50 mls) and the free acid liberated by the addition of concentrated hydrochloric acid (10 N). Upon addition of the pure 2-amino-N-(1,1-dimethylhexyl)acetamide (5 g), off-white crystals of 2-amino-N-(1,1-dimethylhexyl)acetamide naphthalene-2-sulphonate were immediately deposited. The crystals were filtered and dried in vacuo, m.p. 173° C.

EXAMPLE 37—Anti-tetrabenazine test

Female albino mice were grouped, six per cage. Compounds of formula (I) as the respective salt in saline solution were administered orally, thirty minutes prior to the administration of tetrabenazine, 50 mg/kg, i.p. The animals were scored according to the method of V. G. Vernier, H. M. Hanson and C. A. Stone: Psychosomatic medicine, ch. 80, (1962), p. 683.

The results of the test are illustrated in the following table:

| Compound of Example No. & respective salt used | Anti-depressant activity, approx. $ED_{50}$ values, (mg/kg), p.o. | |
|---|---|---|
| | Ptosis | Sedation |
| 2, hydrogen oxalate | 3.5 | 2.3 |
| 4, hydrogen oxalate | 5 | 10.6 |
| 3, hydrogen oxalate | 6.92 | 5.69 |
| 5, hydrogen oxalate | 20 | 10 |
| 8, hydrogen succinate | 3.8 | 2.7 |
| 6, hydrogen fumarate | 18.7 | 9.5 |
| 11, hydrogen fumarate | 5 | 5 |
| 9, hydrogen fumarate | 6 | 7.5 |
| 12, hydrogen succinate | 8 | 2.5 |

EXAMPLE 38—Acute toxicity tests

Several groups of mice were treated with specific doses of compounds of formula (I) as orally administered salts in saline solution. After treatment of each group with a different dose of a specific compound the number of mice dead in each group within two days was noted. Statistical calculations gave the $LD_{50}$ value in milligrammes per kilogramme mouse bodyweight, p.o. for the specific compound. The $LD_{50}$ value is the lethal dose required to kill half of the treated animals.

The procedure was repeated with other groups of mice for other compounds of formula (I). The following table illustrates the results obtained:

| Compound of Example No. & respective salt used | $LD_{50}$ mg/kg., p.o. |
|---|---|
| 3, hydrogen oxalate | >2000 |
| 4, hydrogen oxalate | 1113 |
| 2, hydrogen succinate | 571 |
| 5, hydrogen oxalate | 536 |
| 7, hydrogen fumarate | 1000 |
| 8, hydrogen succinate | 500 |
| 11, hydrogen fumarate | 575 |

EXAMPLE 39

| A Tablet | In one tablet |
|---|---|
| 2-Amino-N-(1,1-dimethylhexyl)acetamide hydrogen succinate | 163.4 mg. |
| Lactose B.P. | 103.6 mg. |
| Maize Starch, B.P. | 25.0 mg. |
| Povidone K30, B.P.C. | 5.0 mg. |
| Magnesium Stearate | 3.0 mg. |

The 2-amino-N-(1,1-dimethylhexyl)acetamide hydrogen succinate, Lactose and Maize Starch were mixed together and then granulated using a solution of the Povidone in purified water. The granules were dried, mixed with the magnesium stearate and then compressed to produce tablets each weighing 300 mg.

163.4 mg. of 2-Amino-N-(1,1-dimethylhexyl)acetamide hydrogen succinate is equivalent to 100 mg. of the free base 2-amino-N-(1,1-dimethylhexyl)acetamide.

Povidone K30 is the trade name of a certain grade of polyvinyl pyrrolidone marketed by Gaff Chemicals Ltd. It is used as a tablet binder.

EXAMPLE 40

| A Capsule | |
|---|---|
| 2-Amino-N-(1,1-dimethylhexyl)acetamide hydrogen succinate | 163.4 mg. |
| Maize Starch, B.P. | 50.0 mg. |
| Lactose, B.P. | 35.4 mg. |

-continued

| A Capsule | |
|---|---|
| Magnesium Stearate | 1.2 mg. |

The 2-Amino-N-(1,1-dimethylhexyl)acetamide hydrogen succinate, Lactose, Starch and magnesium stearate were mixed in a powder blender and then filled into hard gelatin capsules. Each capsule weighed 250 mg.

EXAMPLE 41

| An Injection | | |
|---|---|---|
| 2-Amino-N-(1,1-dimethylhexyl)acetamide hydrogen succinate | | 163.4 mg. |
| Water for Injections | to | 2.0 mls. |

The 2-amino-N-(1,1-dimethylhexyl)acetamide hydrogen succinate was dissolved in 90% of the available water for injections and then diluted to the required volume.

The solution was sterilized by passage through a membrane filter of 0.22 μm pore size and the filtrate was collected in a sterile receiver. The solution was filled into sterile ampoules under aseptic conditions, each ampoule containing 2 mls. The ampoules were sealed by subsequent fusion of the glass.

EXAMPLE 42

| A Suppository | |
|---|---|
| 2-Amino-N-(1,1-dimethylhexyl)acetamide hydrogen succinate | 163.4 mg. |
| Suppository base (Massa Esternium C) to | 2.0 mg. |

The suppository base was melted at around 40° C. and the 2-amino-N-(1,1-dimethylhexyl)acetamide hydrogen succinate as a fine powder was gradually incorporated and mixed until homogeneous. The melted base was then poured into moulds and allowed to set, each suppository weighing 2 mg.

Massa Esternium C is a commercially available suppository base consisting of a mixture of mono-, di- and tri-glycerides of saturated vegetable carboxylic acids, marketed by Henkel International, Dusseldorf.

What we claim is:
1. A glycinamide of formula:

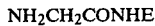

wherein E has seven to nine carbon atoms and is a group:

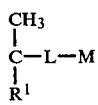

in which $R^1$ is hydrogen or methyl; L and M together form an alkyl or a cycloalkylalkyl group or a pharmacologically and pharmaceutically acceptable salt thereof.

2. A glycinamide as claimed in claim 1 wherein L is alkylene and M is cycloalkyl or unbranched alkyl.

3. A glycinamide as claimed in claim 1 wherein E contains seven to eight carbon atoms.

4. A glycinamide as claimed in claim 1 wherein L is unbranched alkylene.

5. A glycinamide as claimed in claim 1 wherein $R^1$ is methyl;
L is $(CH_2)_n$ in which n is 3, 4 or 5; and
M is methyl; or
$R^1$, C, L and M are cycloalkyl.

6. 2-Amino-N-(1,1-dimethylhexyl)acetamide.
7. 2-Amino-N-(1-methylhexyl)acetamide.
8. 2-Amino-N-(1,1,5-trimethylhexyl)acetamide.
9. 2-Amino-N-(1,1,3-trimethylhexyl)acetamide.
10. 2-Amino-N-(2-cyclopentyl-1,1-dimethylethyl)acetamide.
11. 2-Amino-N-(2-cyclohexyl-1-methylethyl)acetamide.
12. An organic acid addition salt of a compound as defined in claim 1.
13. A dicarboxylic acid addition salt of a compound as defined in claim 1.
14. An addition salt of a compound as defined in claim 1 derived from one of the following acids: hydrochloric, sulphuric, nitric, phosphoric, oxalic, fumaric, maleic, succinic, toluene-p-sulphonic, tartaric, acetic, citric, methanesulphonic, formic, benzoic, malonic, naphthalene-2-sulphonic and benzenesulphonic.
15. 2-Amino-N-(1,1-dimethylhexyl)acetamide hydrogen succinate.
16. 2-Amino-N-(1,1-dimethylhexyl)acetamide methanesulphonate.
17. 2-Amino-N-(1,1-dimethylhexyl)acetamide nitrate.
18. 2-Amino-N-(1,1-dimethylhexyl)acetamide dihydrogen phosphate.
19. 2-Amino-N-(1,1-dimethylhexyl) acetamide benzenesulphonate.
20. A pharmaceutical composition for use as an antidepressant comprising an effective antidepression amount glycinamide of formula:

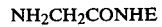

wherein E has seven to nine carbon atoms and is a group:

in which $R^1$ is hydrogen or methyl; L and M together form an alkyl or a cycloalkyl group or a pharmacologically and pharmaceutically acceptable acid addition salt thereof in association with an acceptable carrier therefor.

21. A composition as claimed in claim 20 wherein the carrier is a solid.
22. A composition as claimed in claim 20 wherein the carrier is a liquid.
23. An orally administrable composition according to claim 21.
24. A parenterally administrable composition according to claim 22.
25. A rectally administrable composition according to claim 21.
26. A composition as claimed in claim 23 in the form of an orally ingestable tablet.
27. A composition as claimed in claim 23 in the form of an orally ingestable capsule.
28. A composition according to claim 22 comprising a suspension of a glycinamide or a pharmacologically and pharmaceutically acceptable acid addition salt thereof.

29. A composition according to claim 24 which is a sterile, injectable solution suitable for intravenous, intramuscular or subcutaneous injection.

30. A composition according to claim 25 in the form of a suppository.

31. A composition according to claim 20 in unit dose form.

32. A unit dose composition according to claim 31 containing from 5 mg to 250 mg of a glycinamide or an acid addition salt thereof calculated as the base.

33. A tablet comprising 2-amino-N-(1,1-dimethylhexyl)acetamide or a pharmaceutically or pharmacologically acceptable acid addition salt thereof in association with an acceptable carrier therefor.

34. A tablet according to claim 33 wherein the salt is selected from hydrogen succinate, nitrate, methanesulphonate, dihydrogenphosphate and benzenesulphonate.

35. A method for the treatment of depression in a mammal suffering from such depression comprising the administration to said mammal of a non-toxic, effective, antidepressant dose of a glycinamide of formula:

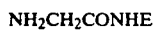

NH₂CH₂CONHE wherein E has seven to nine carbon atoms and is alkylcycloalkyl, cycloalkylalkyl or branched alkyl, or pharmacologically and pharmaceutically acceptable acid addition salt thereof.

36. A method as claimed in claim 35 for the treatment or prophylaxis of neurotic depression.

37. A method as claimed in claim 35 for the treatment or prophylaxis of endogeneous depression.

38. A method as claimed in claim 35 wherein the glycinamide is 2-amino-N-(1,1-dimethylhexyl)acetamide hydrogen succinate.

39. A method as claimed in claim 35 wherein the glycinamide is 2-amino-N-(1,1-dimethylhexyl)acetamide methanesulphonate.

40. A method as claimed in claim 35 wherein the glycinamide is 2-amino-N-(1,1-dimethylhexyl)acetamide dihydrogenphosphate, nitrate or benzenesulphonate.

41. A method as claimed in claim 35 wherein the mammal is man.

42. A method as claimed in claim 35 wherein the glycinamide or the acid addition salt thereof is administered orally.

43. A method as claimed in claim 35 wherein the glycinamide or the acid addition salt thereof is administered at a dose in the range of from 5 mg to 250 mg of the active ingredient per day calculated as the base.

44. A method as claimed in claim 35 wherein the glycinamide or the acid addition salt thereof is administered parenterally or rectally.

* * * * *